US011890097B2

United States Patent
Tai et al.

(10) Patent No.: US 11,890,097 B2
(45) Date of Patent: Feb. 6, 2024

(54) INDUCTIVE DAMPING BRAIN SENSOR

(71) Applicant: California Institute of Technology, Pasadena, CA (US)

(72) Inventors: Yu-Chong Tai, Pasadena, CA (US); Shane S. Shahrestani, Yorba Linda, CA (US)

(73) Assignee: California Institute of Technology, Pasadena, CA (US)

( * ) Notice: Subject to any disclaimer, the term of this patent is extended or adjusted under 35 U.S.C. 154(b) by 387 days.

(21) Appl. No.: 17/179,018

(22) Filed: Feb. 18, 2021

(65) Prior Publication Data

US 2021/0251546 A1    Aug. 19, 2021

Related U.S. Application Data

(60) Provisional application No. 62/978,437, filed on Feb. 19, 2020.

(51) Int. Cl.
*A61B 5/245*    (2021.01)
*A61B 5/00*    (2006.01)
*A61B 5/06*    (2006.01)

(52) U.S. Cl.
CPC .............. *A61B 5/245* (2021.01); *A61B 5/067* (2013.01); *A61B 5/4839* (2013.01);
(Continued)

(58) Field of Classification Search
CPC ....... A61B 5/245; A61B 5/067; A61B 5/4839; A61B 5/6803; A61B 5/684; A61B 5/7246; A61B 2562/0223; A61B 5/02014; A61B 5/0265; A61B 5/7282; A61B 2505/01; A61B 2505/05; A61B 5/02042; A61B 5/0537; A61B 5/4064; A61B 5/6842; A61B 5/6814
See application file for complete search history.

(56) References Cited

U.S. PATENT DOCUMENTS 6,746,785 B1    6/2004 Werner
8,801,646 B2    8/2014 Han et al.
(Continued)

OTHER PUBLICATIONS

Ramrakhyan et al., "Design and Optimization of Resonance-Based Efficient Wireless Power Delivery Systems for Biomedical Implants", IEEE Transactions on Biomedical Circuits and Systems, vol. 5, No. 1, Feb. 2011.
(Continued)

*Primary Examiner* — Colin T. Sakamoto
(74) *Attorney, Agent, or Firm* — Kilpatrick Townsend & Stockton LLP

(57) ABSTRACT

Medical diagnostic devices and related methods of use are described in which one or multiple coils in a sensor, each coil connected with an RLC circuit and frequency counter, are held against a patient's head at predetermined cranial locations. Frequencies of the RLC circuit are measured and compared against those taken from known, control heads, to determine whether there is a medical problem and what type of problem. In some instances, too high of frequencies can reveal pooled blood in the head, a sign of hemorrhagic stroke, while too low of frequencies imply lack of blood supply, a sign of ischemic stroke. A head-mountable frame can assist a first responder in securing and guiding the coils and, along with fiducials, allow for automatic comparison of frequencies with the correct control data.

17 Claims, 15 Drawing Sheets

(52) U.S. Cl.
CPC ............ *A61B 5/6803* (2013.01); *A61B 5/684* (2013.01); *A61B 5/7246* (2013.01); *A61B 2562/0223* (2013.01)

(56) References Cited

U.S. PATENT DOCUMENTS

| | | |
|---|---|---|
| 2009/0112115 A1 | 4/2009 | Huang et al. |
| 2011/0193575 A1 | 8/2011 | Rubinsky et al. |
| 2011/0245707 A1 | 10/2011 | Castle et al. |
| 2013/0123585 A1 | 5/2013 | Kang |
| 2014/0358016 A1 | 12/2014 | Shapira et al. |
| 2015/0339421 A1 | 11/2015 | Srinivasan et al. |
| 2016/0343497 A1 | 11/2016 | Clark et al. |
| 2017/0319099 A1 | 11/2017 | Levinson et al. |
| 2018/0064364 A1 | 3/2018 | Oziel et al. |
| 2018/0230538 A1 | 8/2018 | Stamova-Kiossepacheva et al. |
| 2018/0239430 A1 | 8/2018 | Tadi et al. |
| 2020/0082926 A1 | 3/2020 | Tai et al. |

OTHER PUBLICATIONS

PCT/US2019/050654 , "International Preliminary Report on Patentability", dated Mar. 25, 2021, 9 pages.

PCT/US2021/018560 , "International Search Report and Written Opinion", dated May 6, 2021, 17 pages.

"How to Use Vscan to Measure Urinary Bladder", GE Healthcare, Available online at: https://www.youtube.com/watch?v=35Lda53ZuK0, Aug. 7, 2015, 3 pages.

"LDC1612, LDC1614 Multi-Channel 28-Bit Inductance to Digital Converter (LDC) for Inductive Sensing", Texas Instruments, Available online at: http://www.ti.com/lit/ds/symlink/ldc1612.pdf, Mar. 2018, 67 pages.

Beynon , "A Glimmer of Hope for a Devastating Complication", Blood, vol. 129, No. 22, Jun. 1, 2017, pp. 2952-2953.

Gabriel et al., "Electrical Conductivity of Tissue at Frequencies Below 1 Mhz", Physics in Medicine and Biology, vol. 54, 2009, pp. 4863-4878.

Garcia-Martin et al., "Non-Destructive Techniques Based on Eddy Current Testing", Sensors, vol. 11, No. 3, 2011, pp. 2525-2565.

Giovangrandi et al., "Ballistocardiography—A Method Worth Revisiting", Conference Proceedings, IEEE Engineering in Medicine and Biology Society, Aug. 2011, pp. 4279-4282.

Grieten , "FibriCheck Beat-to-Beat Accuracy Compared with Wearable ECG in Broad Dynamic Range", Available online at: https://www.fibricheck.com/fibricheck-beat-to-beat-accuracy-compared-with-wearable-ecg-in-broad-dynamic-range/12, Jun. 20, 2019, 17 pages.

Lin , "Radiation Risk from Medical Imaging", Mayo Clin. Proc., vol. 85, No. 12, Dec. 2010, pp. 1142-1146.

Nabavi et al., "Design Strategies for Eddy-Current Displacement Sensor Systems: Review and Recommendations", IEEE Sensors Journal, vol. 12, No. 12, Dec. 2012, pp. 3346-3355.

Oberhauser , "Optimizing L Measurement Resolution for the LDC161X and LDC1101", Texas Instruments, Available online at: http://www.ti.com/lit/an/snoa944/snoa944.pdf, Feb. 2016, 9 pages.

PCT/US2019/050654 , "International Search Report and Written Opinion", Nov. 8, 2019, 10 pages.

Robertson et al., "Clinical Evaluation of a Portable Near-Infrared Device for Detection of Traumatic Intracranial Hematomas", Journal of Neurotrauma, vol. 27, No. 9, Sep. 2010, pp. 1597-1604.

PCT/US2021/018560 , "International Preliminary Report on Patentability", dated Dec. 14, 2021, 16 pages.

INDUCTIVE DAMPING BRAIN SENSOR

CROSS-REFERENCES TO RELATED APPLICATIONS

This application claims the benefit of U.S. Provisional Application No. 62/978,437, filed Feb. 19, 2020, which is hereby incorporated by reference in its entirety for all purposes.

STATEMENT AS TO RIGHTS TO INVENTIONS MADE UNDER FEDERALLY SPONSORED RESEARCH AND DEVELOPMENT

NOT APPLICABLE

BACKGROUND

1. Field of the Art

Embodiments of the present invention generally relate to diagnostic instruments, implements, and processes using magnetic field sensors for in vivo measurements. Specifically, they relate to medical devices that distinguish between excess fluid in a brain (a possible hemorrhagic stroke), or lack thereof (a possible ischemic stroke), through measuring resonant frequency and damping changes in an electrical circuit coupled with a magnetic field through the brain.

2. Description of the Related Art

There are two major types of brain strokes. The first is hemorrhagic, in which a vessel ruptures in the brain and leads to excessive bleeding. This can compress areas of the brain and prevent adequate perfusion, leading to cell death. The second type is ischemic, in which an embolus, thrombus, or plaque block a blood vessel and lead to decreased blood flow and cell death.

These two types of strokes are extremely time dependent and have vastly different treatments. For example, for a hemorrhagic stroke, treatments include administering a drug to counteract blood thinners, draining blood from the subject's brain through surgery, clamping an aneurysm through surgery, filling the aneurysm through endovascular embolization, performing surgery to remove an arteriovenous malformation (AVM), or stereotactically focusing radiation at a blood vessel malformation. In contrast, for an ischemic stroke, treatments include administering recombinant tissue plasminogen activator (tPA) or performing surgery to remove a clot.

If a hemorrhagic stroke is mistaken for an ischemic stroke and treated as such, for example by administering blood thinners, then the patient can bleed out. That is, the patient can bleed uncontrollably and die. It can be critical for responders distinguish between a hemorrhagic and ischemic stroke lest they make the problem worse.

Current means for diagnoses includes computed tomography (CT) scans and/or magnetic resonance imaging (MRI) imaging of a patient's head. Both of these methods are expensive and take precious time. Additionally CT scans use ionizing radiation to image the brain; studies have shown that up to 2% of the cancers that arise each year could be due to CT scan radiation.

There is a need in the art for alternative technologies and methods to distinguish between hemorrhagic and ischemic strokes, as well as detect abnormal fluid densities in the brain.

BRIEF SUMMARY

A medical diagnostic device is described for stroke differentiation and other diagnostics in the brain. The device includes a multi-coil sensor having corresponding resistive, inductive, and capacitive (RLC) circuits and frequency counters attached to respective coils. When positioned at a cranial position on a subject's head, a frequency of the RLC circuit is measured and compared with frequencies taken with the sensor from one or more known, nominal heads. If the frequency is too high, then a hemorrhagic stroke is indicated. If the frequency is too low, then an ischemic stroke is indicated. Power measurements can also be taken to determine damping, or resistivity, in the brain.

The device can be moved from location to location on the head, coupled with a wearable frame that ensures accurate positioning. The frame can include fiducial elements read by the device so that it automatically determines where its position is on the head and looks up, from electronic memory, associated frequencies for the position.

Some embodiments of the present invention are related to an inductive sensor apparatus for brain diagnostics, such as stroke triage, including a first sensor coil connected with a first resistive, inductive, and capacitive (RLC) circuit and first frequency counter, a second sensor coil connected with a second RLC circuit and second frequency counter, the second sensor coil having a larger or smaller diameter than the first sensor coil, the first and second sensor coils forming a sensor unit, a memory storing control values derived from prior sensor coil measurements of one or more normal brains in vivo, each control value associated with a corresponding cranial location, a computer processor operatively connected with a machine-readable non-transitory medium embodying information indicative of instructions for causing the computer processor to perform operations including generating measure values based on outputs from the first and second frequency counters when the sensor unit is at a cranial location, determining the cranial location at which the measured values are associated, retrieving, from the memory, control values associated with the cranial location, comparing the measured values to the control values to generate deltas, comparing the deltas to a positive threshold and a negative threshold associated with each cranial location to ascertain an exceedance, the exceedance having a sign and a magnitude, and outputting an indication based on the sign of the exceedance, and an indicator or display connected with the computer processor for the indications.

The operations can further include combining an exceedance from the first sensor coil with an exceedance from the second sensor coil to generate the indication. The indication can include the magnitude of the exceedance.

The apparatus can further include a position gauge attached to the sensor unit, wherein the determining of the cranial location at which the measured values are associated includes reading from the position gauge. It can further include a head-mounting frame including fiducial markers indicating cranial locations, wherein the position gauge is configured to identify cranial locations based on the fiducial markers. The apparatus can further include an attachment point on the head-mounting frame configured to releasably connect with the sensor unit. The attachment point can be configured to guide the first and second coils of the sensor unit in a direction normal (perpendicular) from a surface at the cranial location.

The apparatus can further include an accelerometer or gyroscope connected with the sensor unit and configured to determine the cranial location at which each measured value is taken. The operations can further include generating a matrix of exceedances based on measured values from multiple cranial locations. The operations can further include rendering an image based on the matrix of exceedances. The apparatus can further include a temperature sensor connected with the computer processor, wherein the operations further comprise compensating the measured values for temperature.

The second sensor coil can be coaxial around a common axis with the first sensor coil. An exceedance based upon a frequency higher than a control value can indicate a hemorrhagic stroke, and an exceedance based upon a frequency lower than a control value can indicate an ischemic stroke Some embodiments are related to a method of diagnosing an issue in a subject's brain, such as identifying and distinguishing between an ischemic and hemorrhagic stroke, the method including reading a measured value from a first frequency counter on a first resistive, inductive, and capacitive (RLC) circuit connected with a first sensor coil, reading a measured value from a second frequency counter on a second RLC circuit connected with a second sensor coil, the second sensor coil being coaxial around a common axis with the first sensor coil and having a larger or smaller diameter than the first sensor coil, the first and second sensor coils forming a sensor unit, the sensor unit held to a subject's head, determining a cranial location at which the measured values are read, retrieving, from a memory, control values associated with the cranial location, comparing the measured values with the control values to generate deltas, comparing each delta of the deltas to a positive threshold and a negative threshold in order to ascertain an exceedance, the exceedance having a sign and a magnitude, and indicating, to a user, a possible hemorrhagic or ischemic stroke based on the sign of the exceedance.

The method can further include indicating, to the user, the magnitude of the exceedance. The determining of the cranial location can include reading from a position gauge. The method can further include moving the sensor unit in a direction normal from a surface at the cranial location. The determining of the cranial location can include reading from an accelerometer or gyroscope connected with the sensor unit. The method can further include generating a matrix of exceedances corresponding to multiple cranial locations and rendering an image based on the matrix of the exceedances.

Some embodiments are related to a method of diagnosing an issue, such as a stroke, in a subject's brain, the method including holding, at a cranial location of a subject's head, a sensor unit, the sensor unit including a first sensor coil connected with a first resistive, inductive, and capacitive (RLC) circuit and first frequency counter and a second sensor coil connected with a second RLC circuit and second frequency counter, activating the sensor unit through an apparatus that compares measured values based on frequencies from the sensor unit to stored control values associated with the cranial location, generates deltas based on the comparison, compares the deltas to positive and negative thresholds associated with the cranial location to ascertains exceedances, each exceedance having a sign and a magnitude, reading an indication from the apparatus based on a sign of an exceedance, and treating the subject based on the exceedance.

The exceedance can indicate a hemorrhagic stroke, the method further including treating the subject by administering a drug to counteract blood thinners, draining blood from the subject's brain through surgery, clamping an aneurysm through surgery, filling the aneurysm through endovascular embolization, performing surgery to remove an arteriovenous malformation (AVM), or stereotactically focusing radiation at a blood vessel malformation.

The exceedance can indicate an ischemic stroke, the method further including treating the subject by administering recombinant tissue plasminogen activator (tPA), or performing surgery to remove a clot.

An exceedance based upon a frequency higher than a control value can indicate a hemorrhagic stroke, wherein an exceedance based upon a frequency lower than a control value can indicate an ischemic stroke.

The exceedance can indicate brain cancer, the method further including performing surgery to remove a tumor, administering radiotherapy, or administering chemotherapy. The exceedance can indicate hydrocephelus, the method further including performing surgery to place a shunt, or draining fluid from the brain. The exceedance can indicate a vascular abnormality, the method further including performing surgery to correct the vascular abnormality. The exceedance can indicate neurodegeneration, the method further including administering a drug to the subject.

DETAILED DESCRIPTION

An inductive sensor for the human brain compares measured values to those acquired from known, control brains taken in the same position on the head. Any measured value outside of normal ranges can indicate too much or too little blood in the measured area. Too much blood in the brain is a symptom of a hemorrhagic stroke, while too little is a symptom of an ischemic stroke. The sensor can let the user know which type of stroke may be and approximately where it is located.

Unlike a traditional electronic crack detection (ECD) sensor used in industry, which consist of a bridge circuit that measures its sensor coil impedance, present embodiments have the sensor coil paired with a capacitor to form an electrical resonant circuit. When a conductive target, such as blood, is placed in front of the coil, eddy currents are generated in the target and produce a counteracting magnetic field. This counteracting magnetic field causes a decrease in the coil inductance, or equivalently, a rise in the coil resonant frequency that can be measured by a precise frequency counter.

The same counteracting magnetic field in the target also imposes an electromotive force that impedes the current flow in the coil, thus increasing the sensor coil's alternating current (AC) resistance. The change in coil resistance can be determined by measuring the power dissipation in the coil with a precise power meter. The parallel resistance (R) of the resonant inductive-capacitive (LC) tank is inversely related to the coil's AC resistance by R.

U.S. Patent Application Publication No. US 2020/0082926 A1, published Mar. 12, 2020, further describes fundamentals of an inductive damping sensor and is incorporated herein by reference.

A technical advantage of the resonant circuit is low power consumption. This can be of great importance for wearable or otherwise portable, battery-powered sensors. Assuming the skull can be modeled as a flat, two-layer structure (see FIG. 14A), then the coil's AC resistance is related to the tissue conductivity implicitly and can be modeled by a set of analytical solutions.

Figure 1:
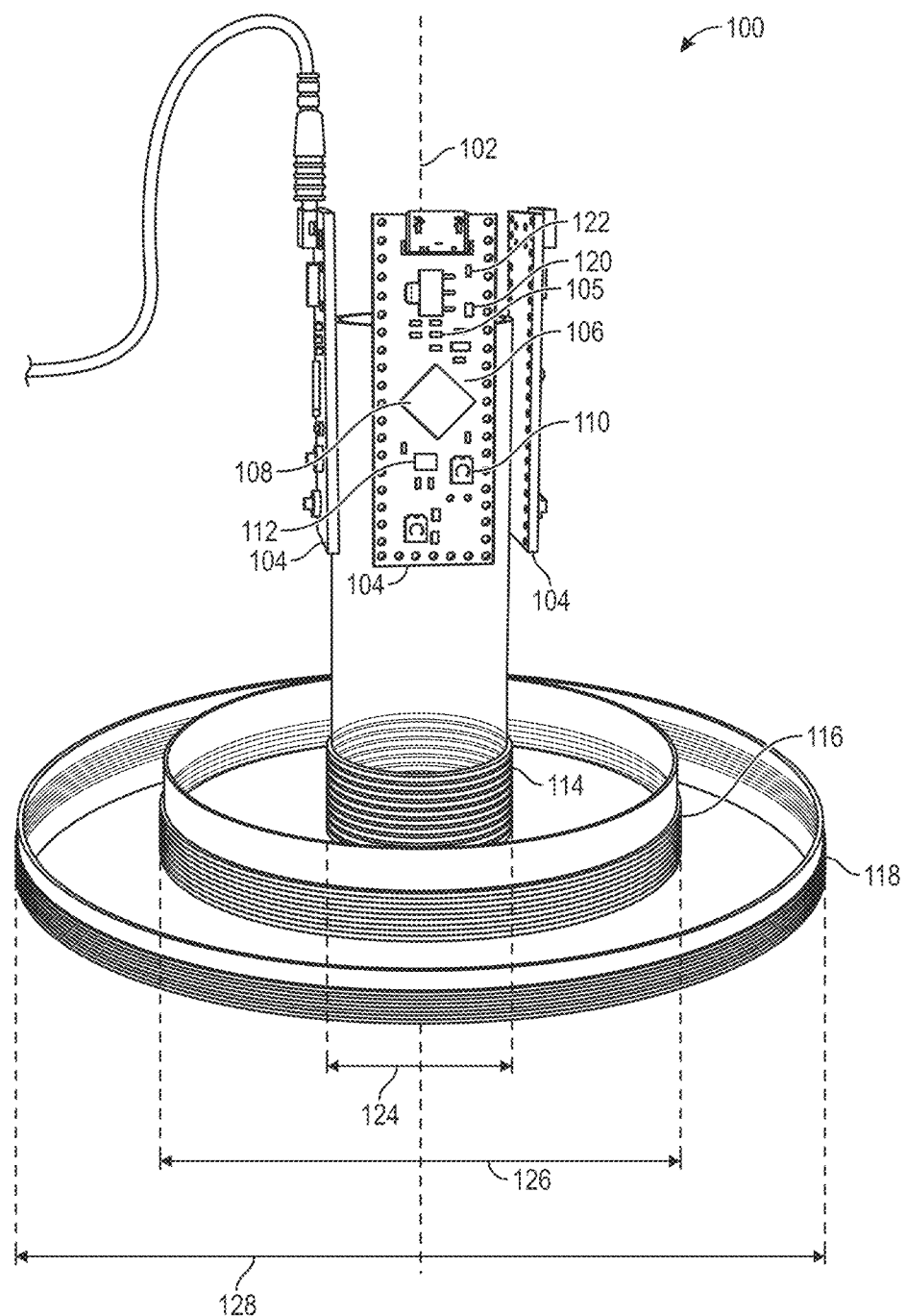
FIG. 1 illustrates a multi-coil diagnostic device in accordance with an embodiment.

FIG. 1 illustrates multi-coil diagnostic device 100 in accordance with an embodiment. Around central, common axis 102 are situated coaxial sensor coils 114, 116, and 118. Each sensor coil 114, 116, and 118 has an insulated wire coiled in a tight helical shape so that each wrap round has the same diameter. Sensor coil 114 has the smallest diameter, diameter 124. Sensor coil 116 has medium diameter 126, and sensor coil 118 has large diameter 128. Sensor coils 114, 116, and 118 are referred to as small, medium, and large coils.

The design of the sensor may use a variety of sizes and shapes. One or multiple coils may be arranged together to form a device. The coils may be of different diameters, heights, and/or lengths. The "diameter" may then refer to a nominal or average diameter. The coils can have different thicknesses of wire and different shapes (e.g., solenoid, circular, spiral, planar, frustum). Variously sized coils may allow for varying spatial, temporal, and depth resolution.

No common axis is necessary for the coils to share. The coils can be offset from one another, and no two coils need share the same axis. There can be more than two coils, such as three, four, five, or 'N' coils. None need be concentric or share an axis.

The coils may be made of metal or other conductor with each wound insulated from each other by an insulator.

Magnetic shielding may be used to protect the coils from internal or external signals. Magnetic shielding may be of any size, thickness, or material so long as it serves the purpose of increasing the signal-to-noise ratio or improving characteristics of the device.

In the exemplary embodiment, each coil is electrically connected to a separate unit 104 of analog and digital processing components, each with a resistive, inductive, and capacitive (RLC) circuit 106 and frequency counter 110.

Memory 112 stores programming instructions and control values derived from prior sensor coil measurements of one or more normal brains in vivo, along with corresponding cranial location data. That is, data from previous measurements of known brains with the same or similar type of coil is averaged or otherwise processed to distill normal ranges of frequency and power loss measurements for particular positions on the brains. Although different people's heads exhibit different magnetic inductances based on age, gender, demographics, and even diet or time since sleep, there are normal ranges of inductance that are relatively stable. A stroke, especially a massive one, changes the inductance significantly due to the heavy influence of iron atoms in hemoglobin on magnetic permeability.

Computer processor 108 reads and writes from memory 112 and executes instructions described herein. The instructions cause the processor to read measured values from the power meter and frequency counter 110, compare them with control values associated with the cranial location, calculate deltas, and compare the deltas to positive and negative thresholds associate with the cranial location to ascertain an exceedance.

A "computer processor" includes any type of miniature electronic device with arithmetic, logic, and/or control circuitry for performing central processing, or a general or specialized digital circuit that performs translation or reconveying of digital signals using logic or other components, or as otherwise known in the art. For example it can include a traditional processor, a programmable logic controller (PLC), etc.

A "delta" is a difference between two values, or as otherwise known in the art.

An "exceedance" includes a value that is above a maximum threshold or below a minimum threshold, or as otherwise known in the art. An exceedance can have a sign and a magnitude. The sign can indicate whether the exceedance is above a positive threshold or below a negative one.

The computer processor can output the exceedance itself or a simplified indication. Indicator 105 can light up or audibly emit a sound to tell an operator of the exceedance. A display may show much more data, as described further below. The processor, memory, and other elements can be incorporated on a commercial off-the-shelf board.

In prototypes, some of which are described in the figures, the Texas Instruments LDC (inductive to digital converter)

1101 chip was used to convert signals from coils into computer readouts. However, the sampling rate for this LCD 1101 frequency counter IC chip is limited to approximately 40 samples per second. In order to navigate this limitation, heterodyne downshifting was used for a higher frequency readout. If a higher sampling rate is required, the coil voltage can be connected to a frequency mixer and get downshifted to a lower frequency at approximately 1 kHz. Then the low-frequency signal is sampled by an analog-to-digital converter, bandpass-filtered, and conditioned by digital signal processing algorithms to recover the resonant frequency. This method allows a higher sampling rate above 200 samples per second. Each coil is connected to its own LDC 1101 chip, with readout sent to a local computer in series.

Various other types of sensors may be introduced onto the inductive damping sensor, such as accelerometer 122, gyroscopes, piezoelectric sensors, or temperature sensor 120. These devices can be used to improve the overall accuracy or precision of the inductive damping sensor. For example, accelerometer 122 can allow for device positioning and trajectory mapping as the device is moved around the head, while temperature sensor 120 can allow for temperature compensation to increase signal accuracy.

Figure 2:
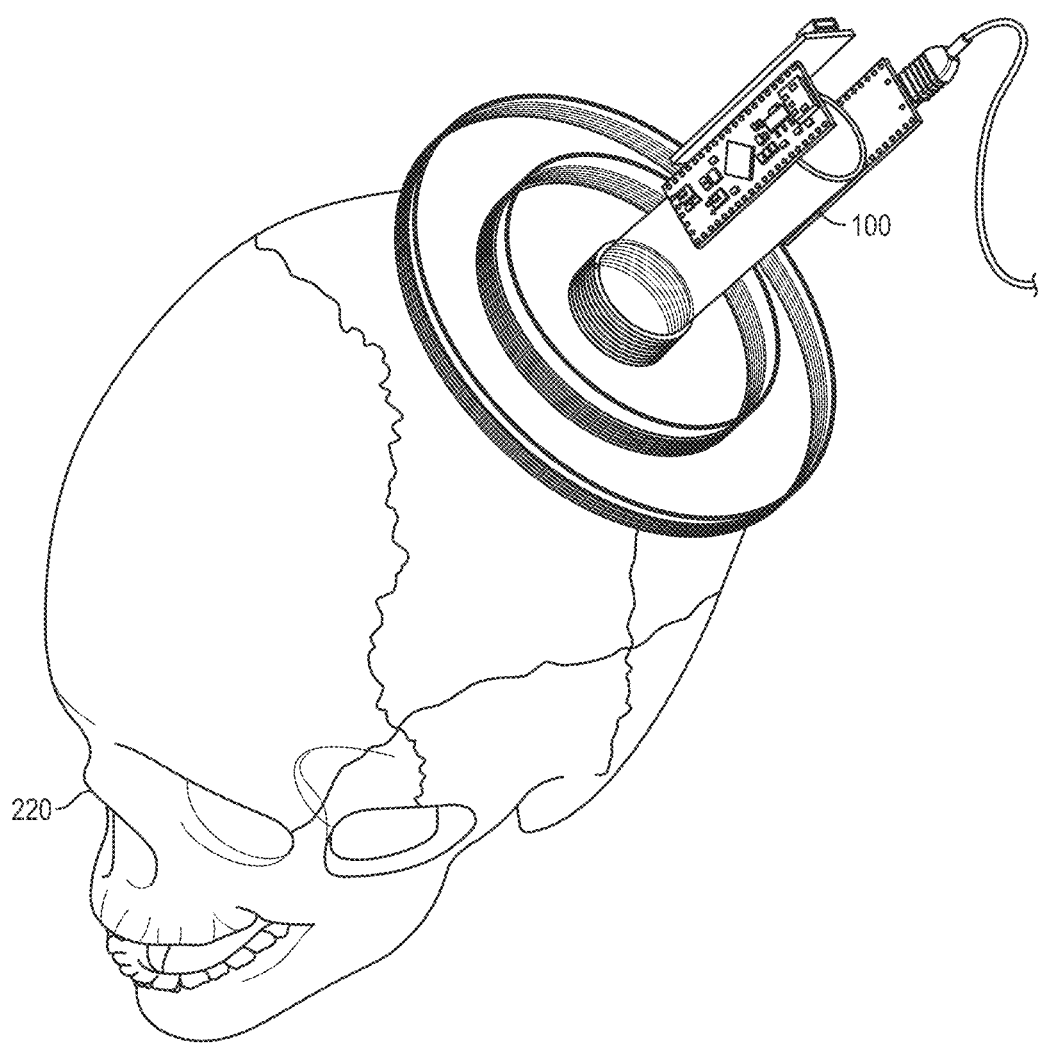
FIG. 2 illustrates the device of FIG. 1 held against a skull of a patient.

FIG. 2 illustrates device 100 being held against patient's cranium 220. The patient may be seated, lying, or in other positions. A first responder, caregiver, physician, or other user may position the device according to predetermined locations and obtain a result in real-time.

Data obtained by the device may be stored on a local, remote, cloud or cell network. Transmission of data may be through the use of a wire, radio frequency (RF) such as BLUETOOTH® compatible communications, infrared, optical, or otherwise. This can allow for remote diagnostics based off of patient data and also the possibility of directly reporting information into an electronic medical record (eMR). This would also allow for consolidation of data for predictive model creation and analysis. Artificial intelligence (AI) machine learning algorithms (e.g., neural networks, support vector machines) can be used to differentiate between different brain conditions and lesions by utilizing the output generated by the device. The algorithms may also be used to predict the depth, location, size, volume, or shape of lesions.

Figure 3:
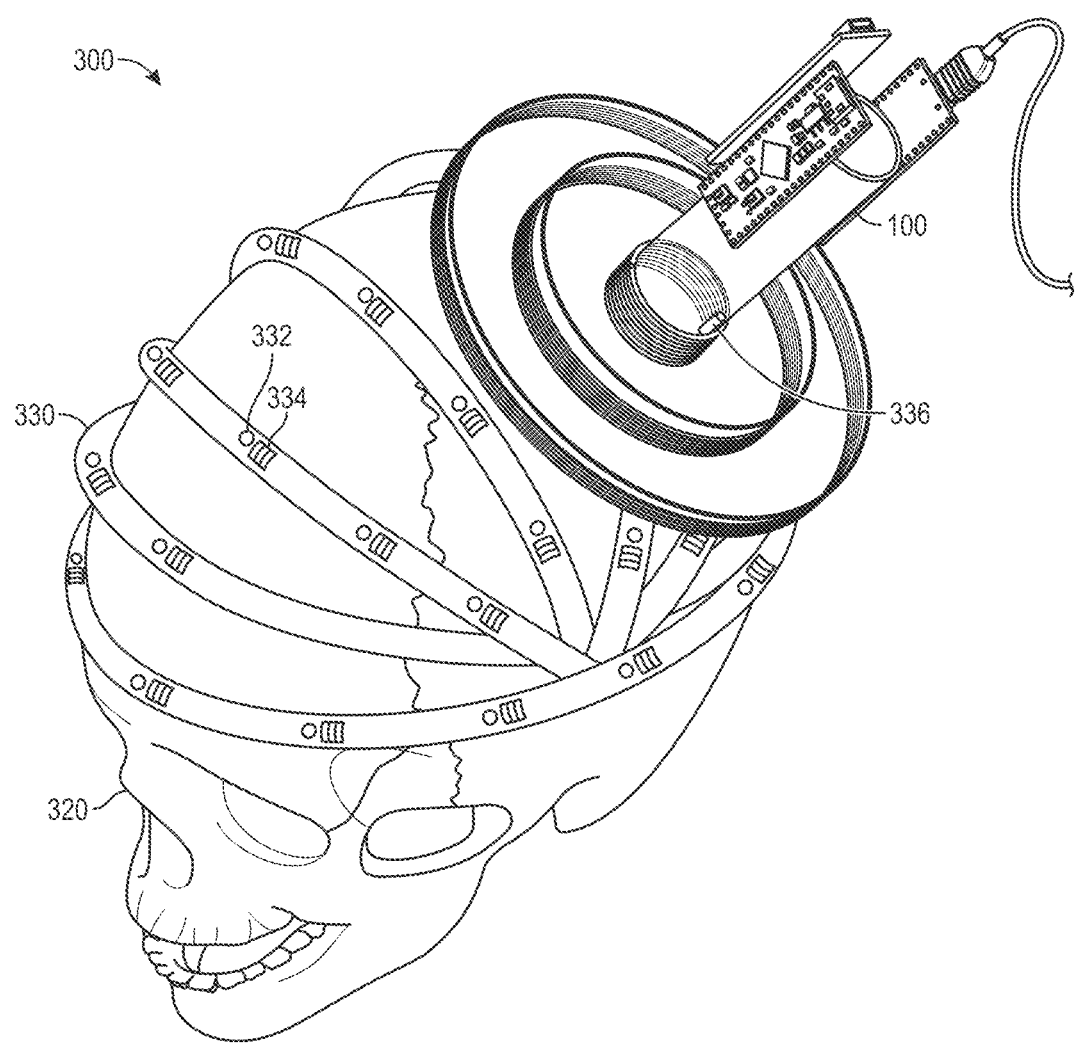
FIG. 3 illustrates the device of FIG. 1 releasably connected with a cranial positioning frame in accordance with an embodiment.

FIG. 3 illustrates head-mounting frame 330 on patient's head 320 to which device 100 is releasably connected, forming connected system 300. Head-mounting frame 330 includes nonconductive, non-magnetic lateral rails on which attachment points 332 are formed. Each attachment point can be a small hole socket, rivet head, or other feature to which a mating connector may be rigidly connected.

Near each attachment point 332 is a fiducial marker 334. Each fiducial marker is different and is associated with a particular position on head-mounting frame 330. The fiducial markers are small barcodes that are read by optical position sensor 336 on device 100, which scans the bar code. The processor on device 100 can read from position sensor 336 and automatically determine where it is on the head, i.e., at what cranial location the coils are positioned. This may be used independently or in conjunction with other means of determining the cranial location, such as by accelerometers or by user data entry.

Head-mounting frame attachment point 332 may facilitate guiding the sensor device radially, i.e., perpendicular to a surface of the head, in order to gather more data from the coils. As the coils are moved closer or farther away from the head, they may detect different features of interest or gain sensitivity for an area of interest to a user.

Certain devices may automatically traverse the head-mounting frame, automatically taking and reporting measurements as it goes. Regardless of whether the device is manual or automatic, the device may have one or multiple points of contact with the head or device frame as scanning occurs.

From multiple points of measurements over and across the head, a matrix of measurements can be taken. Each measurement value is compared with data in the normal range for the corresponding cranial location and plus-minus tolerances or other thresholds, and a matrix of exceedances is generated. The matrix of exceedances can be charted and displayed to a user.

Data acquired may be represented in two-dimensions (2D) or three-dimensions (3D). 3D image production of brain lesions may provide more clear assessments of lesion location, depth, volume, size, and shape.

Figure 4A:
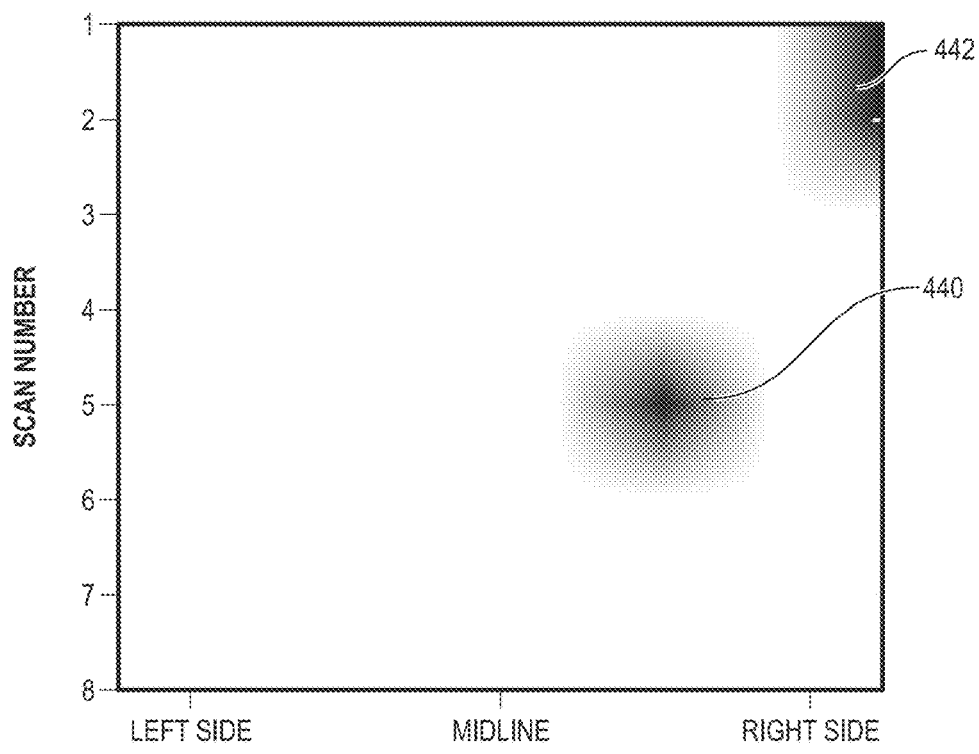
FIG. 4A is a map showing the cranial location of exceedances for a large coil in accordance with an embodiment.
Figure 4B:
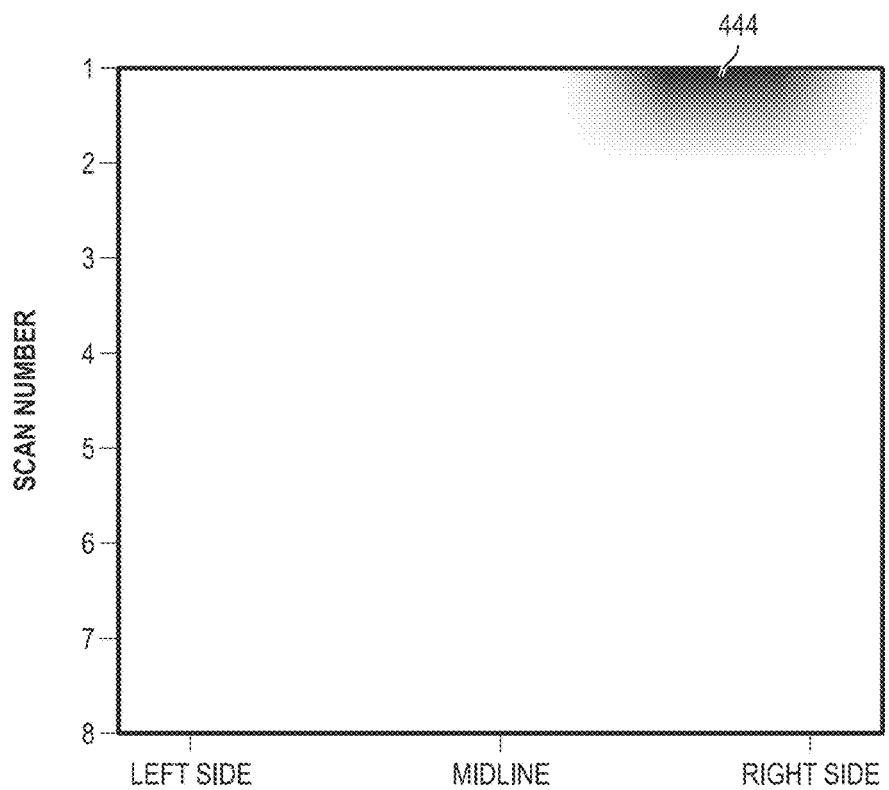
FIG. 4B is a map showing the cranial location of exceedances for a medium coil in accordance with an embodiment.
Figure 4C:
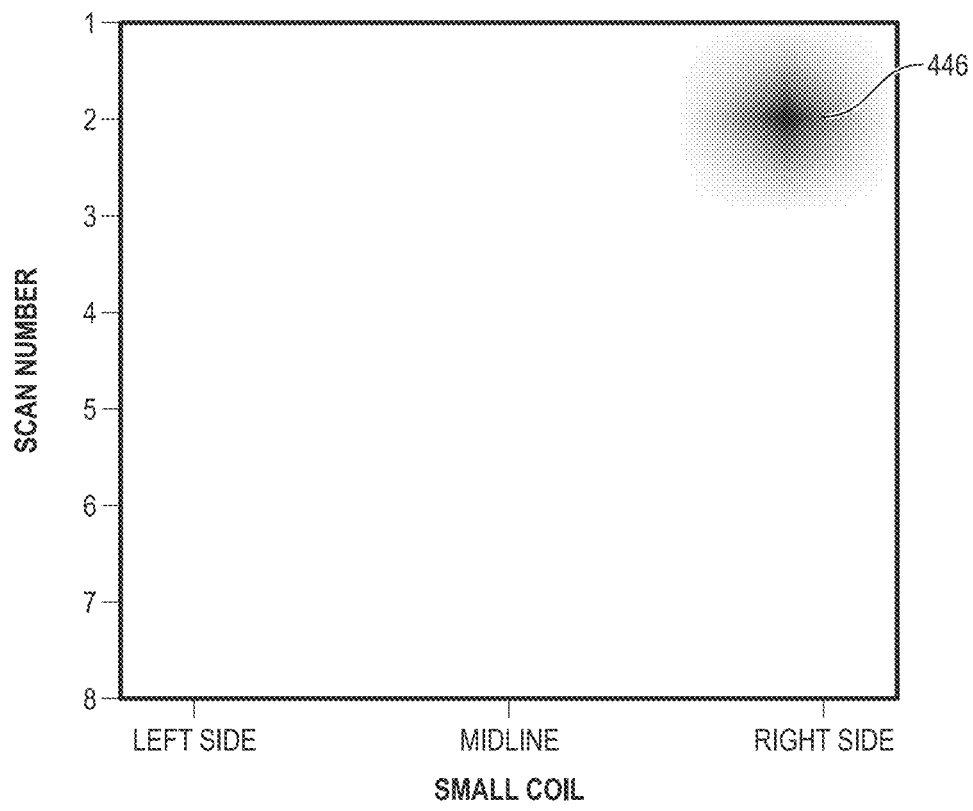
FIG. 4C is a map showing the cranial location of exceedances for a small coil in accordance with an embodiment.

FIGS. 4A-4C are maps showing the cranial locations of exceedances for a large (FIG. 4A), medium (FIG. 4B), and small (FIG. 4C) coils in accordance with an embodiment.

FIG. 4A shows that the large coil picked up anomalies in the upper right hand side and near the center midline. Exceedance 442 is in the upper right, which denotes the right-front of the brain. Exceedance 440 is near the center midline, which denotes the top middle of the brain.

FIG. 4B also shows an anomaly in the top right at exceedance 444. It is slightly inward from where exceedance 442 is on FIG. 4A. Revealingly, no anomaly is detected in the medium coil where exceedance 440 is found in the large coil.

FIG. 4C confirms an anomaly in the top right, at exceedance 446. It is slightly back from where exceedances 442 and 444 are, but close by nonetheless. Like the medium coil, the small coil detects no anomaly where exceedance 440 is found in the large coil.

Figure 5:
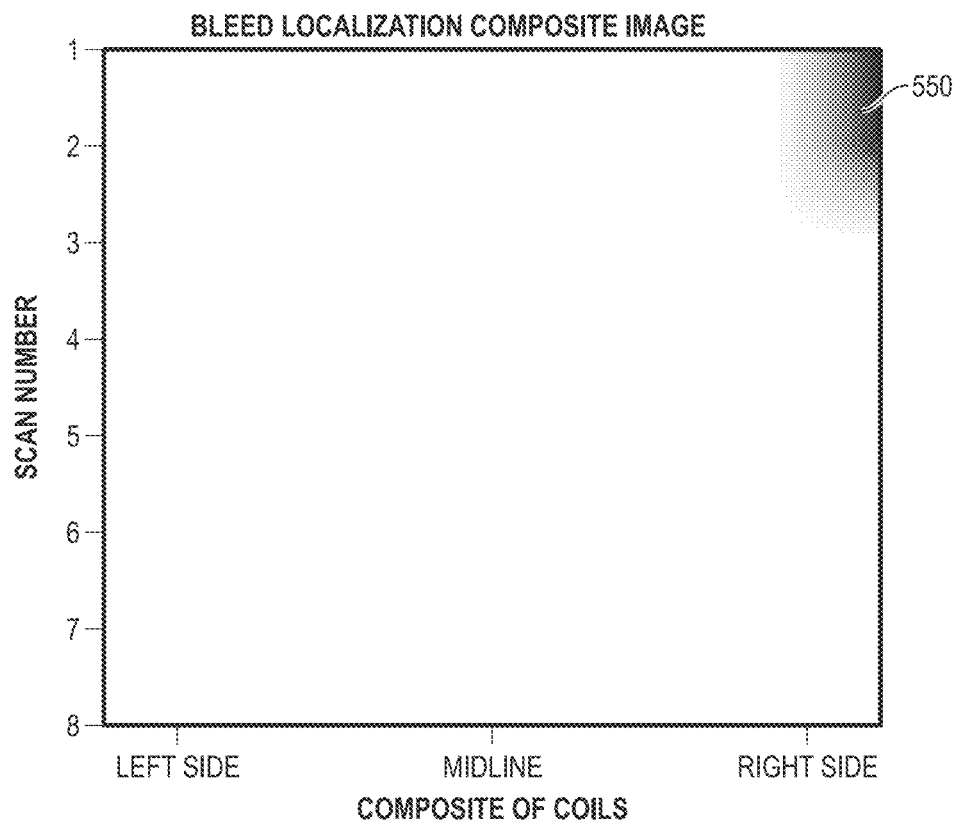
FIG. 5 is a map showing the cranial location of exceedances combined from FIGS. 4A-4C in accordance with an embodiment.

FIG. 5 is a map showing the cranial location of exceedances combined from FIGS. 4A-4C in accordance with an embodiment. The exceedance values, or rather the percentage-based, normalized exceedances from the different matrices, are averaged together to form the combined matrix. The averaged exceedances omit exceedance 440 (FIG. 4A) as an outlier and combine exceedances 442, 444, and 446 from the coils as exceedance 550.

In some embodiments, different weights are given to each of the coils' exceedance values before summing to average. The weights may be based on the relative "antenna pattern"-like lobe strengths from the respective coils. For example, the large coil may have a narrow magnetic field that goes relatively deep into the brain, while the small coil has a wider magnetic field that is shallow.

Figure 6:
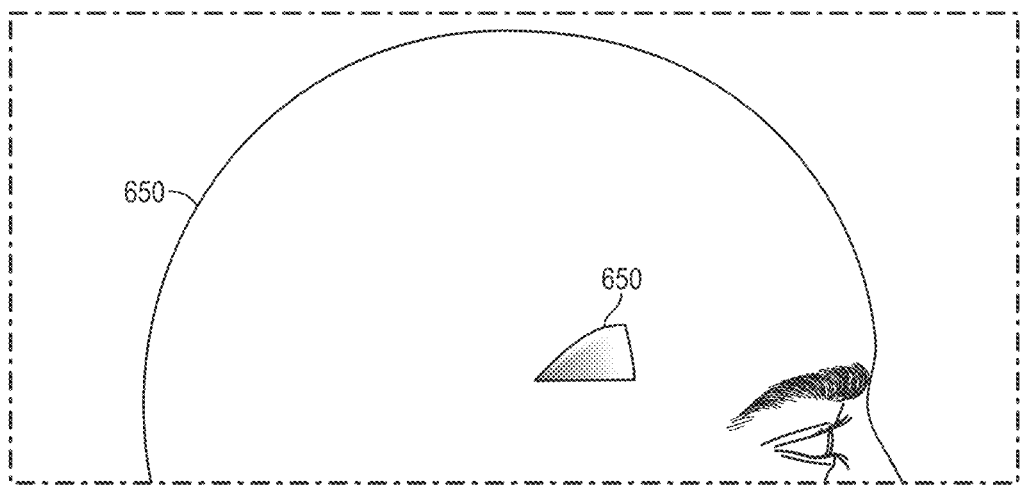
FIG. 6 is a three-dimensional (3D) rendering of a location of the exceedances mapped in FIG. 5.

FIG. 6 is a three-dimensional (3D) rendering 650 of a location of the exceedances on a graphic of a patient's head. Volume 650 is plotted to show a user approximately where there may be a problem in the brain. Data for plotting the volume came from the three different coils.

Figure 7B:
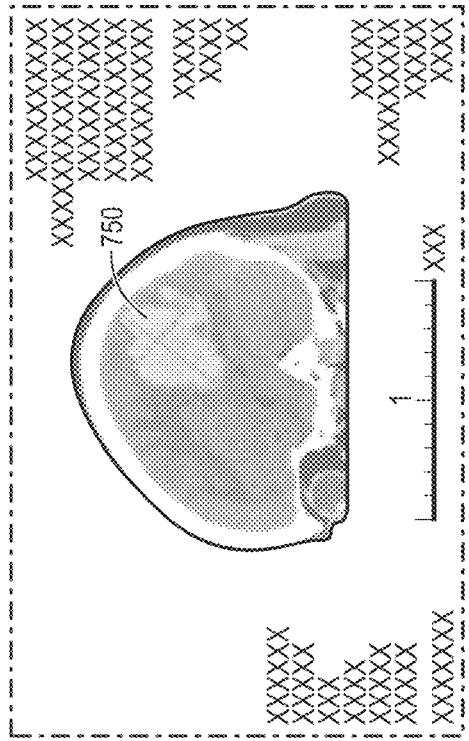
FIG. 7B is a cross section image from a CT scan from the left side of the patient measured for FIG. 6.
Figure 7A:
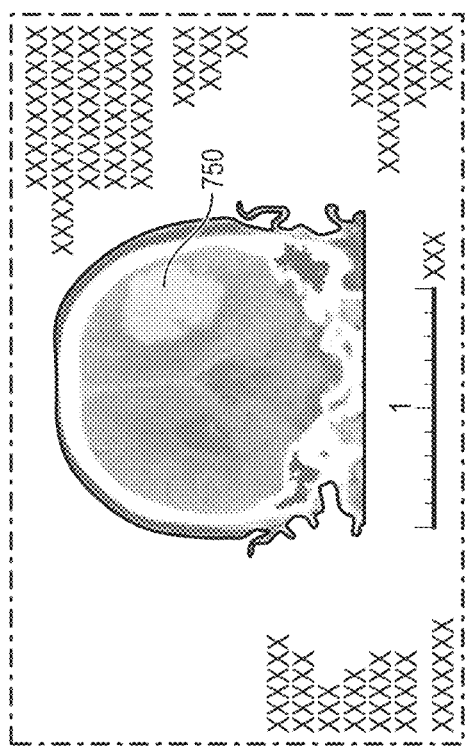
FIG. 7A is a cross section image from a CT scan from the back of the patient whose head was measured for FIG. 6.
Figure 7C:
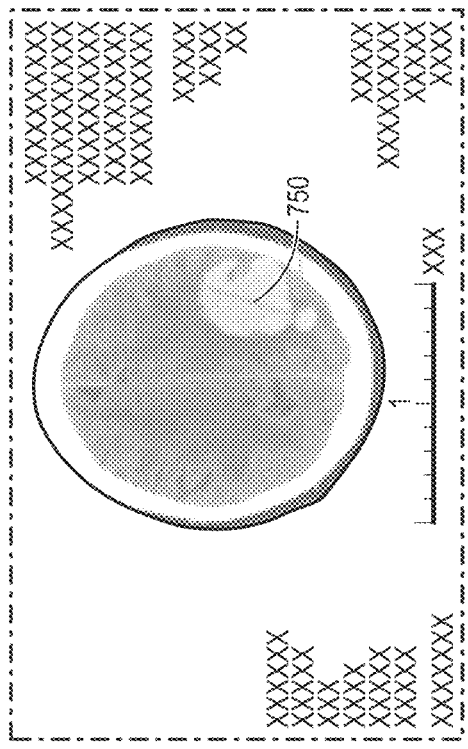
FIG. 7C is a cross section image from a CT scan from the top of the patient measured for FIG. 6.

FIGS. 7A-7C are CT scans for the actual patient from which data for FIGS. 4A-5 were measured. This is the "truth data." The CT scans confirm that there is a problem in the patient's brain, a large volume 750 that is filled with blood. It was caused by a hemorrhagic stroke.

A technical advantage of some embodiments is that they employ relatively simple and low cost coils to achieve a fast diagnosis of whether there is a stroke and what type of stroke it is. The device can be made relatively inexpensively and thus be available more widely, such as in nursing homes and outpatient clinics. In contrast, a CT scanner can cost tens of thousands of U.S. dollars for refurbished equipment to two-and-a-half million for a new machine. MRI machines can cost even more. Both CT and MRI machines require specialized expertise to use. It is hoped that the relatively simplicity of present embodiments may not require much training, and perhaps require no training similar to that of automatic defibrillator machines.

Figure 8:
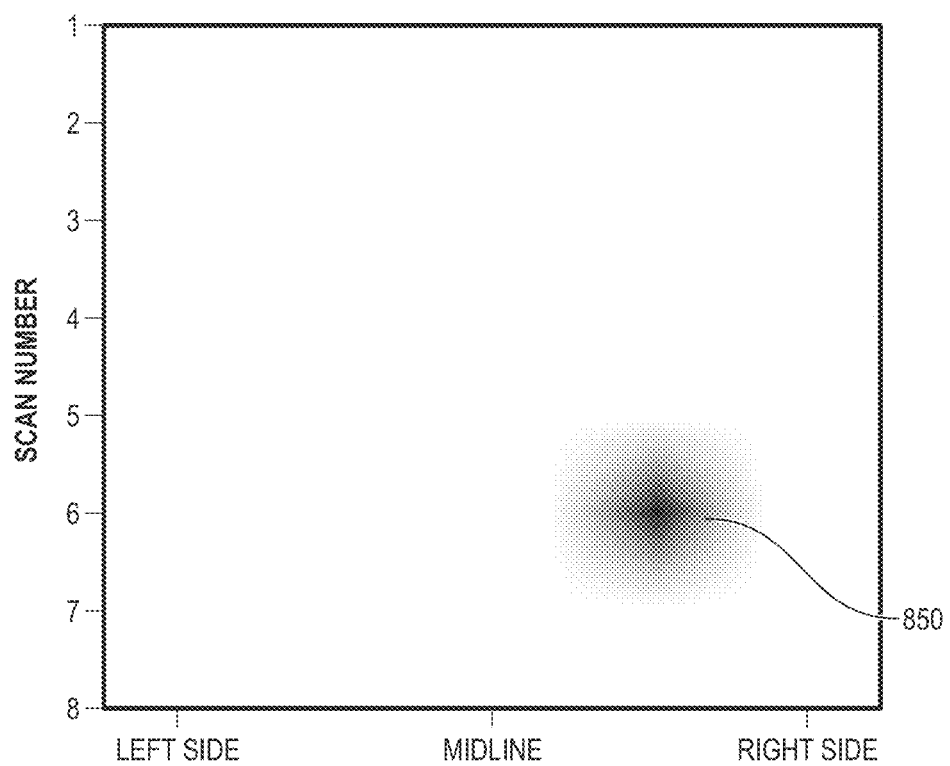
FIG. 8 is a map showing cranial location of exceedances in another patient in accordance with an embodiment.

FIG. 8 is a map showing cranial location of exceedances in another patient in accordance with an embodiment. An anomaly is detected near the midline toward the back, shown as exceedance 850.

Figure 9:
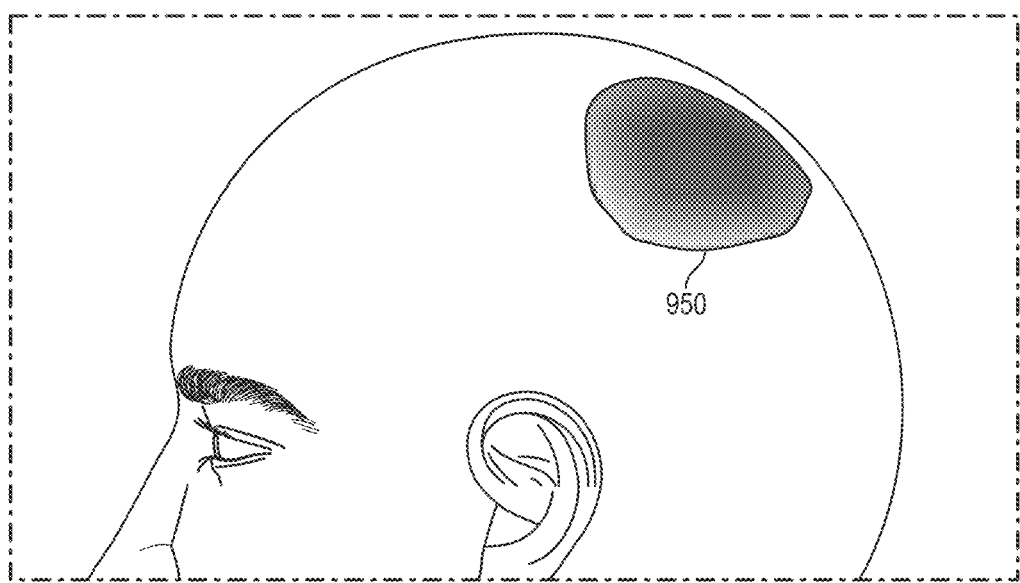
FIG. 9 is a three-dimensional (3D) rendering of a location of the exceedances mapped in FIG. 8.

FIG. 9 is a three-dimensional (3D) rendering of a location of the exceedances mapped in FIG. 8. In this case, the smaller coil, which detects shallower fluid, detected more of an exceedance than the other coils and thus volume 950 of interest is shown closer to the scalp. The 3D rendering can be panned and rotated so that a physician can determine where the blood is located and narrow down what caused it.

Figure 10A:
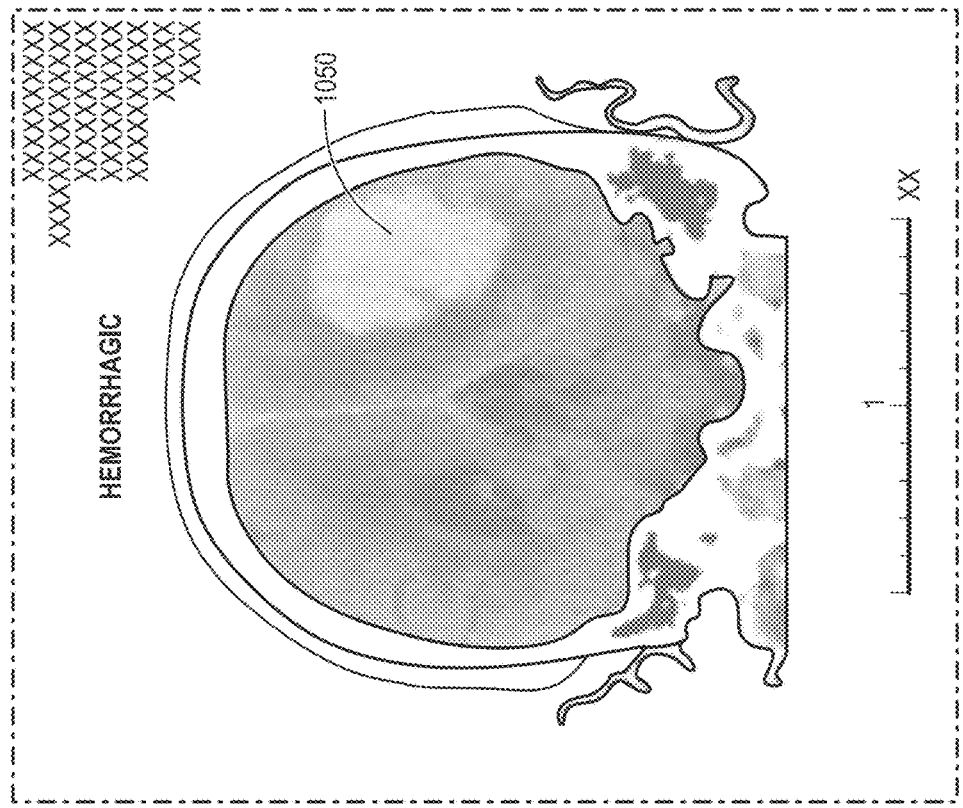
FIG. 10A is a cross section image from a CT scan from the back of the patient whose head was measured for FIG. 8.
Figure 10B:
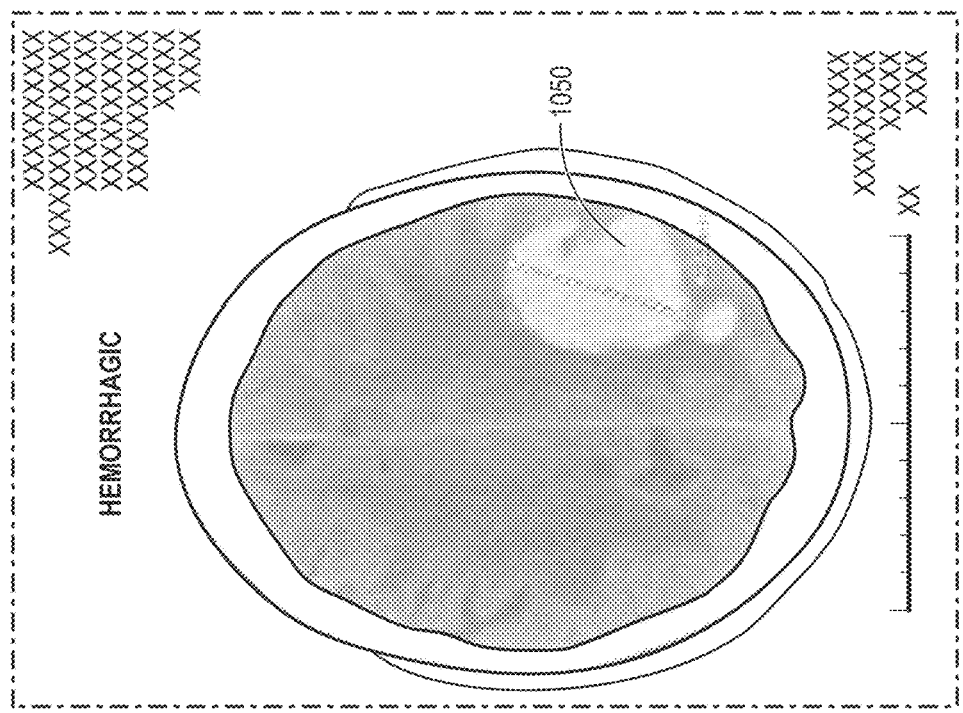
FIG. 10B is a cross section image from a CT scan from the top of the patient measured for FIG. 8.

FIGS. 10A-10B are truth data CT scans of the patient from which data for FIG. 8 was measured. The CT scans confirm that there is a problem in the patient's brain on the right side, a large volume 1050 filled with blood. As indicated in the data, the frequencies were higher than normal, indicating a hemorrhagic stroke.

Figure 11:
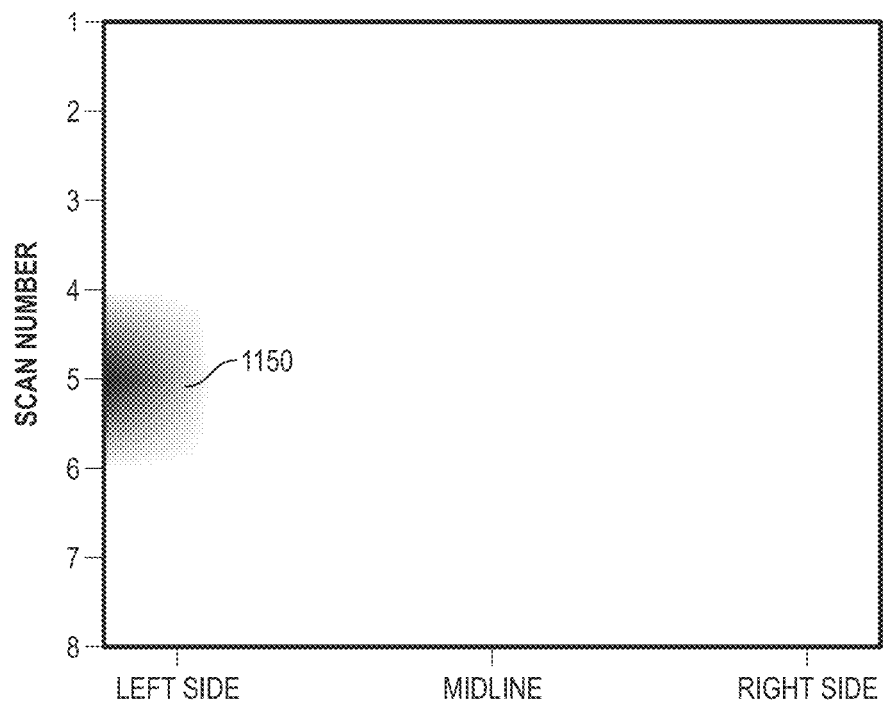
FIG. 11 is a map showing cranial location of exceedances in yet another patient in accordance with an embodiment.

FIG. 11 is a map showing cranial location of exceedances in yet another patient in accordance with an embodiment. An anomaly on the left side near the center is shown as exceedance 1150

Figure 12:
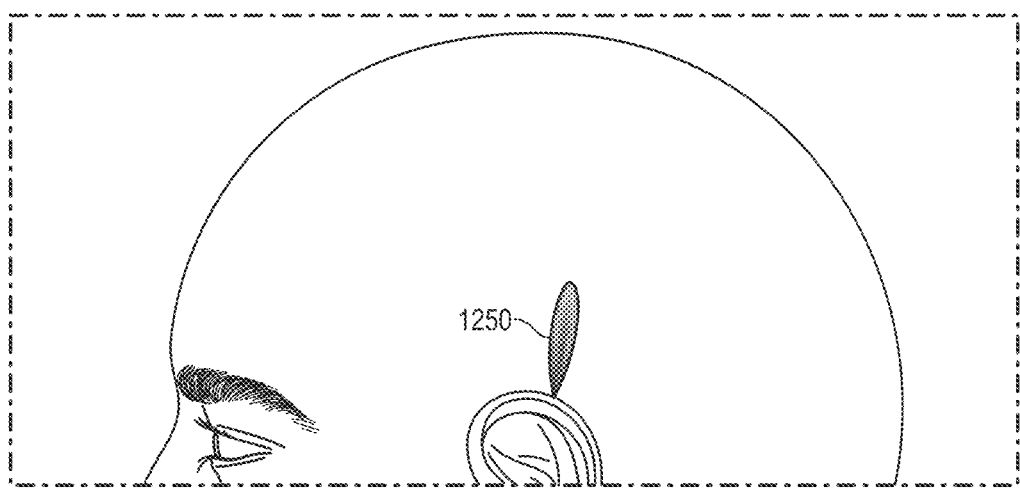
FIG. 12 is a three-dimensional (3D) rendering of a location of the exceedances mapped in FIG. 11.

FIG. 12 is a three-dimensional (3D) rendering of a location of the exceedances mapped in FIG. 11, this time showing region 1250 above the left ear of the patient.

Figure 13B:
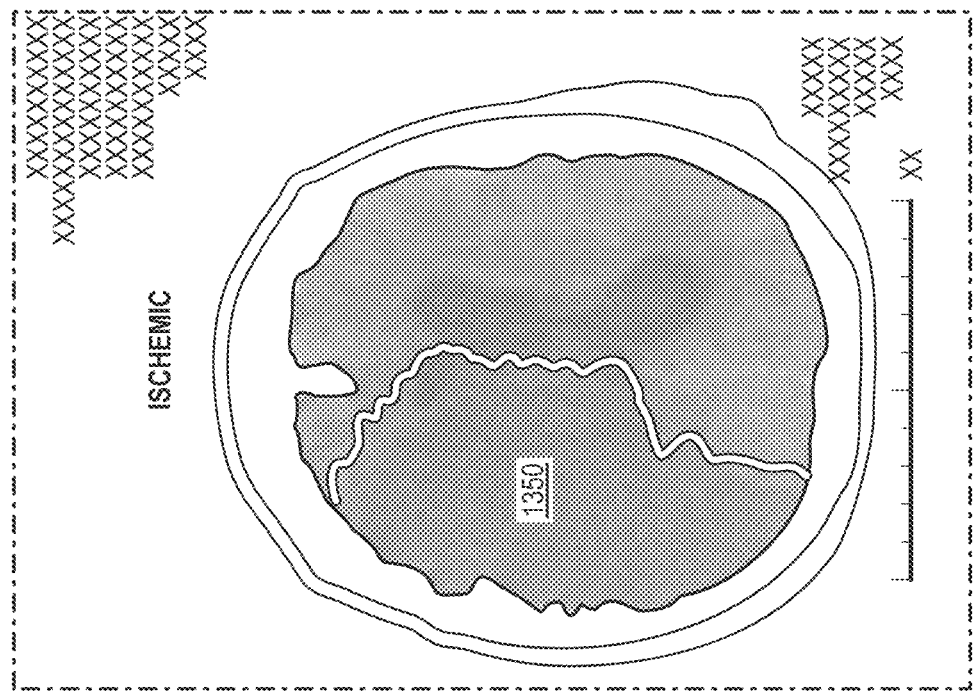
FIG. 13B is a cross section image from a CT scan from the top of the patient measured for FIG. 11.
Figure 13A:
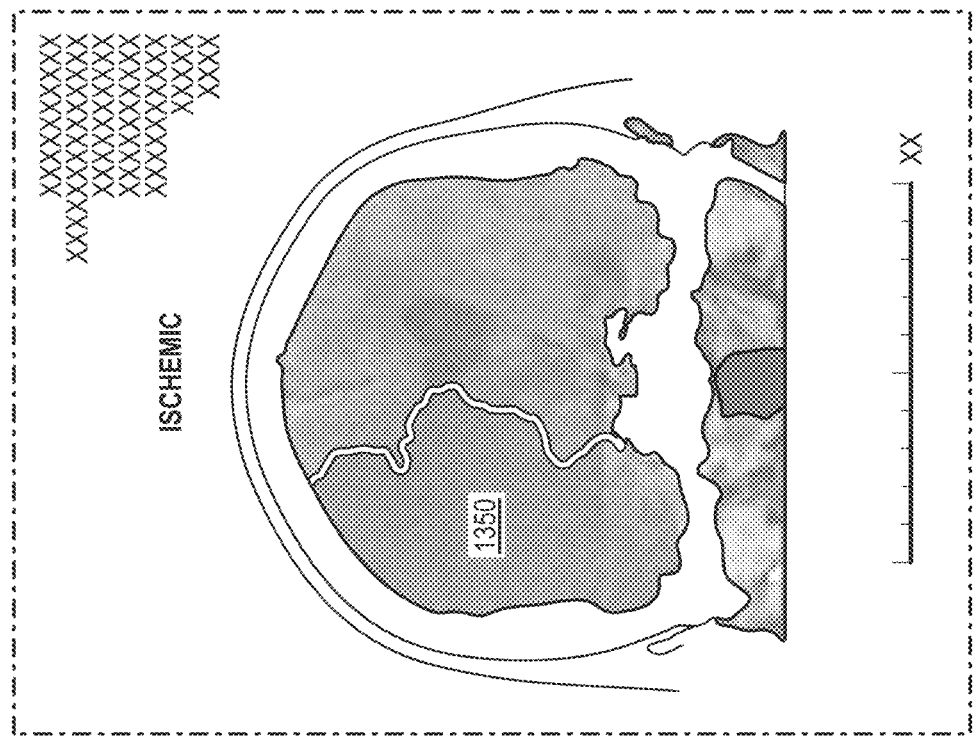
FIG. 13A is a cross section image from a CT scan from the left side of the patient whose head was measured for FIG. 11.

FIGS. 13A-13B are truth data CT scans of the patient from which data for FIG. 11 was measured. The CT scans confirm that there is a problem in the patient's brain on the left side. In this case, it is an extremely large volume 1350 that lacks sufficient blood. The staunched flow reaches all the way to the cranium. The coils detected an issue through a centroid of the volume, which is just over the ear as shown in the previous figure. As indicated in the data, the frequencies were lower than normal, indicating an ischemic stroke. Thus, blood thinners may be an option for this stroke patient.

Figure 14A:
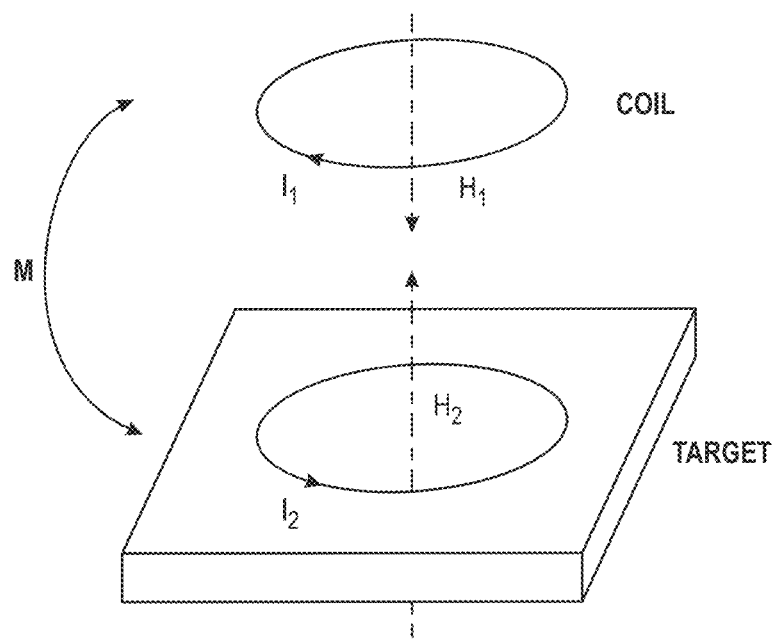
FIG. 14A illustrates magnetic coupling in a model of a coil and target in accordance with an embodiment.

FIG. 14A illustrates magnetic coupling in a model of a coil and target in accordance with an embodiment. The coil is modeled as having current $i_1$ and producing magnetic field Hi. This creates magnetic coupling M between it and a target. The target is a human head, modeled as a flat, two-layer structure with its own current $i_2$ and induced magnetic field Hz. Note that currents $i_1$ and $i_1$ are in opposite directions.

Figure 14B:
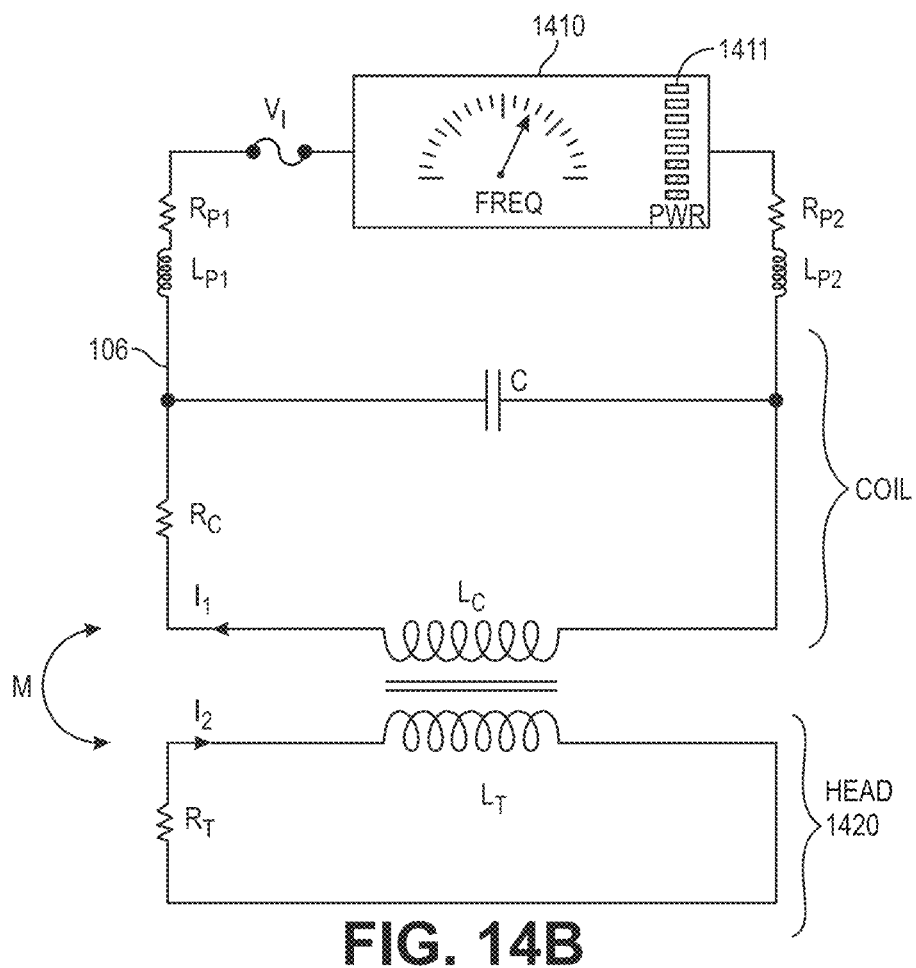
FIG. 14B is an equivalent circuit for the model in FIG. 14A.

FIG. 14B illustrates equivalent circuits for the model in FIG. 14A. RLC circuit 106 includes a coil modeled with current $i_1$ running through inductor Lc with resistance Rc and capacitance C. The coil is connected to a voltage source providing Vi alternating current. Parasitics of connections are modeled as resistances $R_{p1}$ and $R_{p2}$ and inductances $L_{p1}$ and $L_{p2}$.

Frequency counter 1410 and power meter 1411 are shown, from which measured values can be taken, recorded, compared, and used to indicate anomalies. Data may be converted in an analog-to-digital (A/D) converter and read into a computer processor.

The coil is connected through magnetic coupling M to patient head 1420. Head 1420 includes eddy current $i_2$ running through an idealized resistor Rt (target) and inductor Lt.

Figure 15:
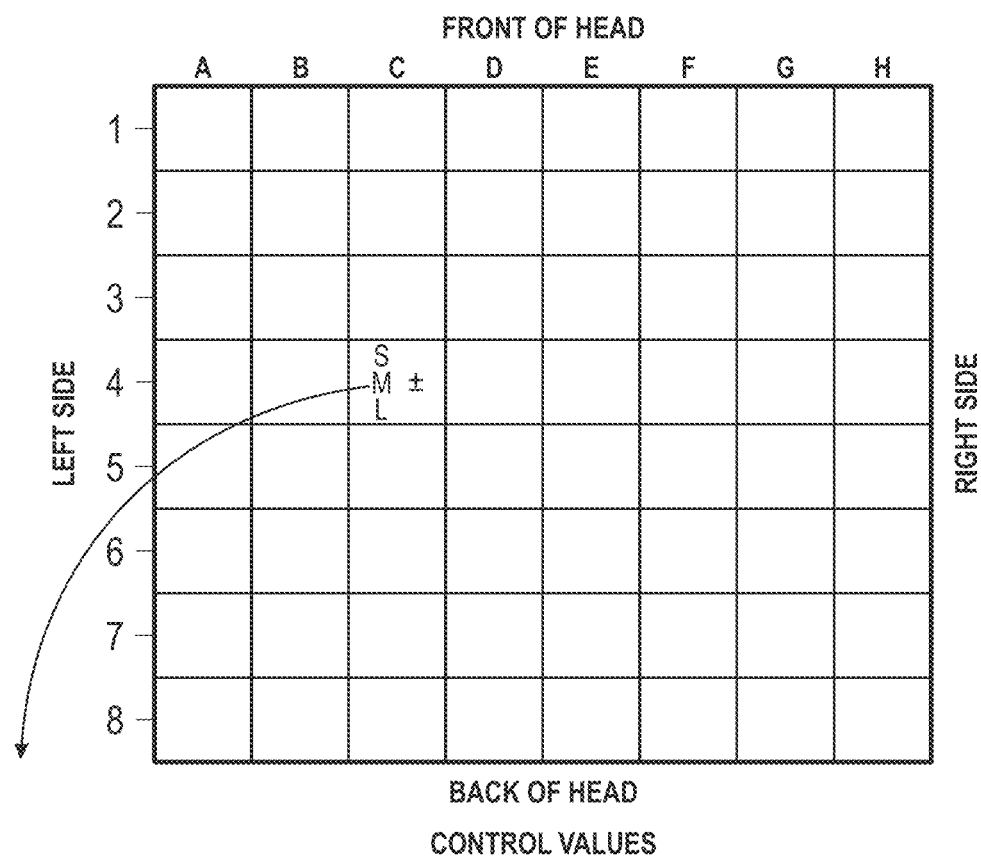
FIG. 15 illustrates reading control values for a particular cranial location from a computer memory in accordance with an embodiment.

FIG. 15 illustrates reading control values for a particular cranial location from a computer memory in accordance with an embodiment. There may be many, many different positions, but for clarity the figure shows an 8×8 grid. Associated with each position are control values for the S(mall), M(edium), and L(arge) coils. Once a cranial position is known, the corresponding values from memory may be extracted and compared with measured values.

Figure 16:
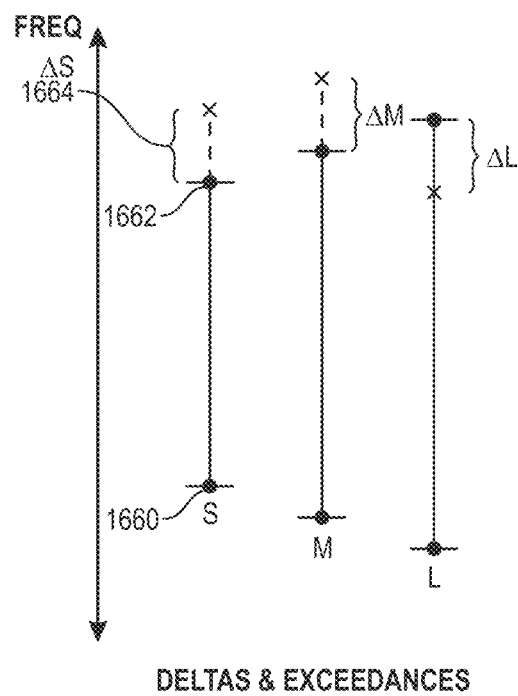
FIG. 16 illustrates the calculation of deltas and exceedances in accordance with an embodiment.

FIG. 16 illustrates the calculation of deltas and exceedances in accordance with an embodiment. The vertical axis is frequency, but the actual measured values can represent calibrated frequency, derived measurements, or other values based on frequency and/or resistance measured in the coils. Data for each of the coils is plotted across the chart.

For the S(mall) coil, the normal range is plotted as minimum control value 1660 and maximum control value 1662. These may correspond to actual values measured in normal brains, or they may be derived from statistical comparisons of many normal (and abnormal) brains and adjusted for standard deviations, tolerances in equipment, etc. An 'X' marks the measured frequency for the coil, which in the case of the small coil is above maximum control value 1662. A difference between the measured value (X) and maximum control value 1662 is calculated as delta 1664, a.k.a. ΔS. Similarly for the other coils, ΔM and ΔL are also calculated.

The deltas ΔS, ΔM, and ΔL are compared against respective thresholds for the cranial location to compute exceedances. For example, ΔS and ΔM are above and outside of the normal ranges by a large margin and thus are classified as exceedances. Meanwhile, ΔL is within the normal range and is not classified as an exceedance.

The exceedances for ΔS and ΔM are positive, that is, above the maximum threshold above the control values. Besides a magnitude, they each have a positive sign to indicate that they are above the control values. This sign may be used to distinguish between a hemorrhagic and ischemic stroke.

Aside from strokes, the sensor may also be used for detecting traumatic brain injury, non-stroke hemorrhages in the brain, arteriovenous malformations (AVMs), benign or malignant brain tumors, and degenerative brain diseases.

Some embodiments can differentiate between lesion subtypes (i.e., ischemic and hemorrhagic strokes) based off whether the measured current, voltage, conductivity, impedance, eddy current, magnetic field, or resistance have increased or decreased with respect to normal brains or with respect to time. This would allow for differentiation between ischemia and a hemorrhage based on the direction and/or magnitude of the sensor signal.

Some embodiments may be scanned in the direction normal to the head (i.e., z-axis) to gain information about a brain lesion. Aside from movements in the direction tangential to the each (i.e., the x-axis and y-axis), the device may be moved in the z-direction to further obtain depth information regarding the lesion. Movement in the z-direction may also allow for varying spatial, temporal, and depth resolution.

To make these measurements, the device may be moved manually, such as being held or controlled by an operator, or the device may be automatically moved by computer controlled motors around the head for scanning. Automation may be due to an internal or external motor.

Figure 17:
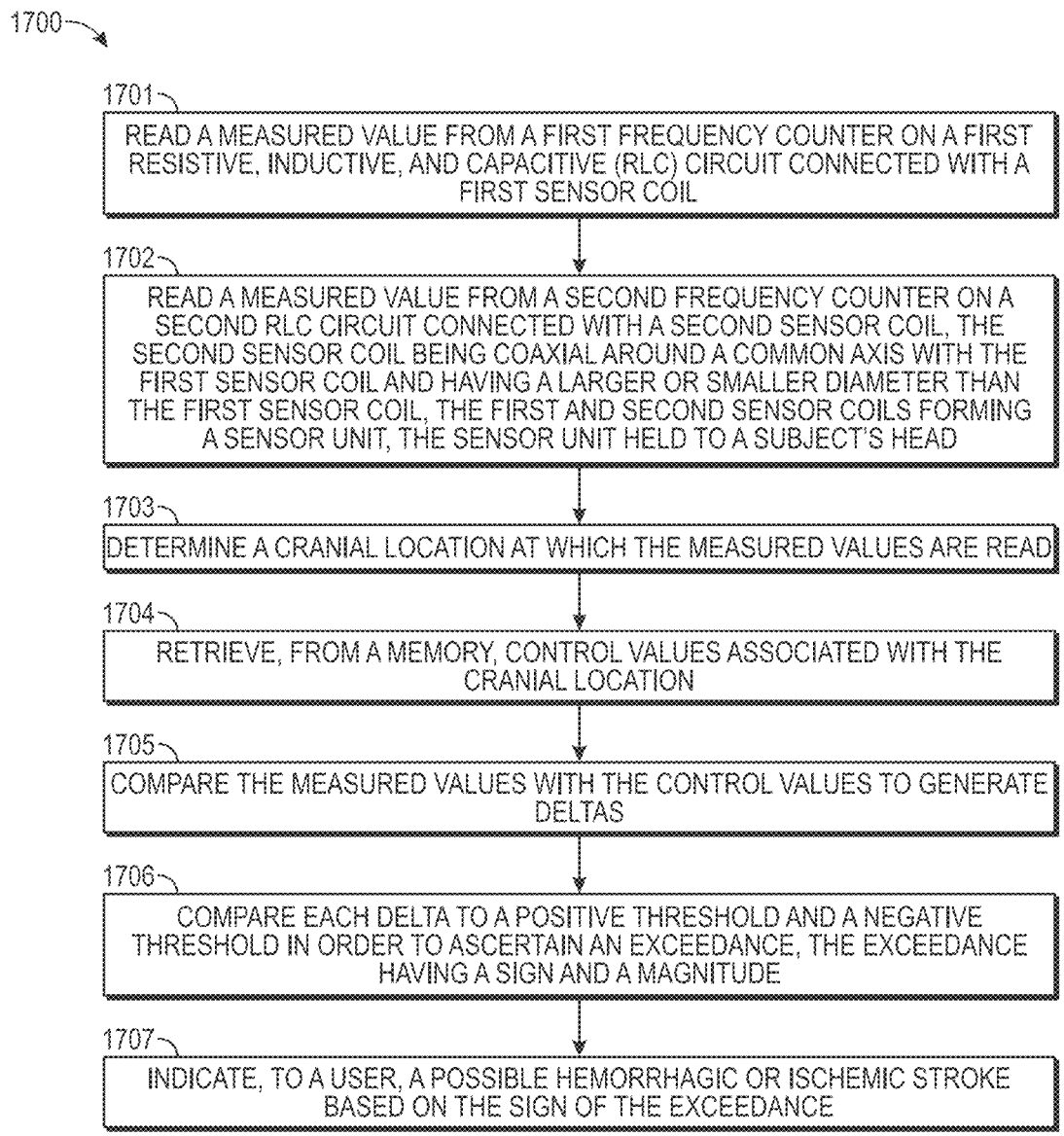
FIG. 17 is a flowchart illustrating a process in accordance with an embodiment.

FIG. 17 is a flowchart illustrating method 1700 of distinguishing between ischemic and hemorrhagic strokes in a subject's brain. In operation 1701, a measured value is read from a first frequency counter on a first resistive, inductive, and capacitive (RLC) circuit connected with a first sensor coil. In operation 1702, a measured value is read from a second frequency counter on a second RLC circuit connected with a second sensor coil, the second sensor coil being coaxial around a common axis with the first sensor coil and having a larger or smaller diameter than the first sensor coil, the first and second sensor coils forming a sensor unit, the sensor unit held to a subject's head. In operation 1703, a cranial location at which the measured values are read is determined. In operation 1704, control values associated with the cranial location are retrieved from a memory. In operation 1705, the measured values are compared with the control values to generate deltas. In operation 1706, each delta is compared to a positive threshold and a negative threshold in order to ascertain an exceedance, the exceedance having a sign and a magnitude. In operation 1707, a possible hemorrhagic or ischemic stroke is indicated to a user based on the sign of the exceedance.

Figure 18:
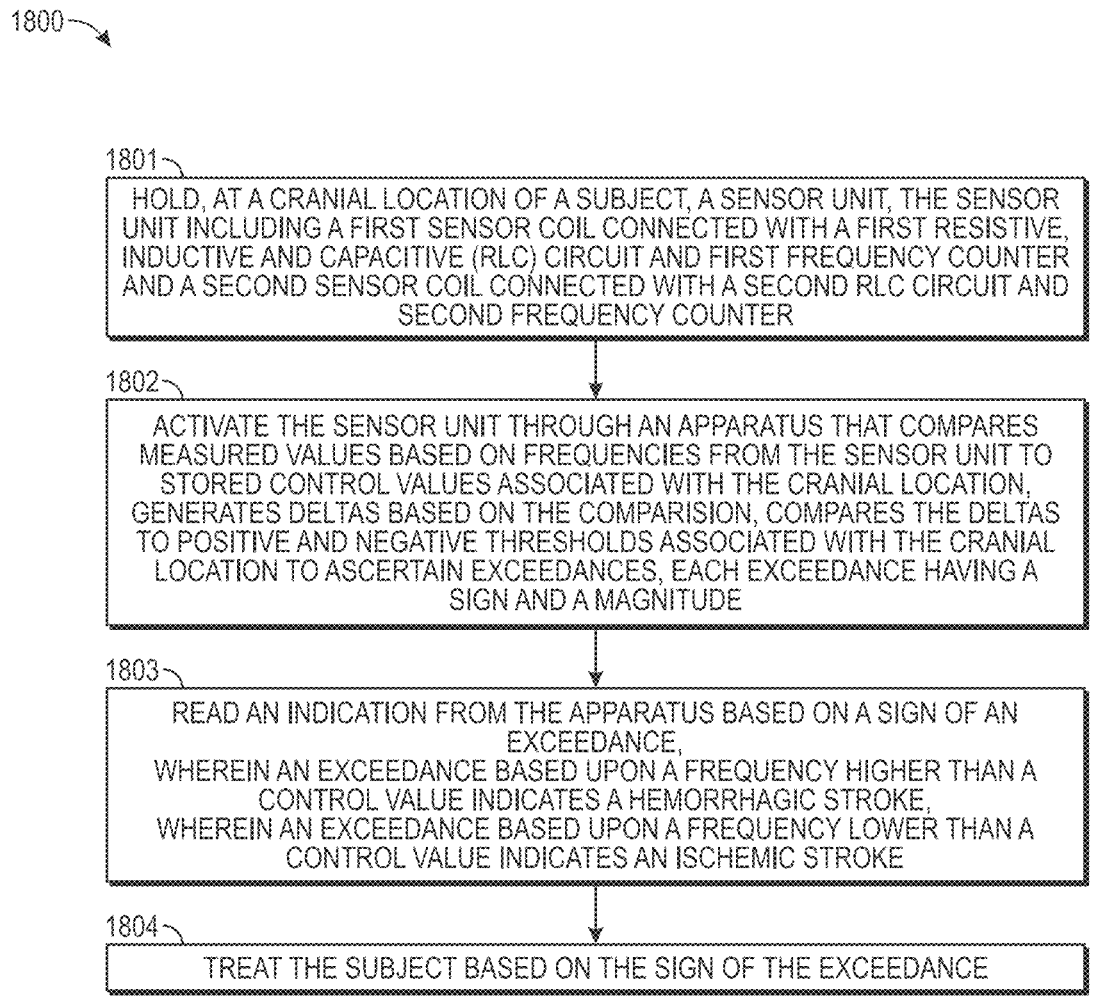
FIG. 18 is a flowchart illustrating a process in accordance with an embodiment.

FIG. 18 is a flowchart illustrating method 1800 of diagnosing a stroke in a subject's brain. In operation 1801, a sensor unit is held at a cranial location of a subject, the sensor unit including a first sensor coil connected with a first resistive, inductive, and capacitive (RLC) circuit and first frequency counter and a second sensor coil connected with a second RLC circuit and second frequency counter. In operation 1802, the sensor unit is activated through an apparatus that compares measured values based on frequencies from the sensor unit to stored control values associated with the cranial location, generates delta based on the comparison, and compares the deltas to positive and negative thresholds associated with the cranial location to ascertain exceedances, each exceedance having a sign and a magnitude. In operation 1803, an indication based on a sign of an exceedance is read from the apparatus, wherein an exceedance based upon a frequency higher than a control value indicates a hemorrhagic stroke, and an exceedance based upon a frequency lower than a control value indicates an ischemic stroke. In operation 1804, the subject is treated based on the sign of the exceedance.

While the foregoing has described what are considered to be the best mode and/or other examples, it is understood that various modifications may be made therein and that the subject matter disclosed herein may be implemented in various forms and examples, and that the teachings may be applied in numerous applications, only some of which have been described herein. It is intended by the following claims to claim any and all applications, modifications and variations that fall within the true scope of the present teachings.

Unless otherwise stated, all measurements, values, ratings, positions, magnitudes, sizes, and other specifications that are set forth in this specification, including in the claims that follow, are approximate, not exact. They are intended to have a reasonable range that is consistent with the functions to which they relate and with what is customary in the art to which they pertain. "About" in reference to a temperature or other engineering units includes measurements or settings that are within ±1%, ±2%, ±5%, ±10%, or other tolerances of the specified engineering units as known in the art.

The scope of protection is limited solely by the claims that now follow. That scope is intended and should be interpreted to be as broad as is consistent with the ordinary meaning of the language that is used in the claims when interpreted in light of this specification and the prosecution history that follows and to encompass all structural and functional equivalents.

Except as stated immediately above, nothing that has been stated or illustrated is intended or should be interpreted to cause a dedication of any component, step, feature, object, benefit, advantage, or equivalent to the public, regardless of whether it is or is not recited in the claims.

It will be understood that the terms and expressions used herein have the ordinary meaning as is accorded to such terms and expressions with respect to their corresponding respective areas of inquiry and study except where specific meanings have otherwise been set forth herein. Relational terms such as first and second and the like may be used solely to distinguish one entity or action from another without necessarily requiring or implying any actual such relationship or order between such entities or actions. The terms "comprises," "comprising," or any other variation thereof, are intended to cover a non-exclusive inclusion, such that a process, method, article, or apparatus that comprises a list of elements does not include only those elements, but may include other elements not expressly listed or inherent to such process, method, article, or apparatus. An element proceeded by "a" or "an" does not, without further constraints, preclude the existence of additional identical elements in the process, method, article, or apparatus that comprises the element.

The Abstract is provided to allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in various embodiments for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus the following claims are hereby incorporated into the Detailed Description, with each claim standing on its own as a separately claimed subject matter.

What is claimed is:

1. An inductive sensor apparatus for brain diagnostics comprising:
   a first sensor coil connected with a first resistive, inductive, and capacitive (RLC) circuit and first frequency counter;
   a second sensor coil connected with a second RLC circuit and second frequency counter, the second sensor coil having a larger or smaller diameter than the first sensor coil, the first and second sensor coils forming a sensor unit;
   a memory storing control values derived from prior sensor coil measurements of one or more normal brains in vivo, each control value associated with a corresponding cranial location;
   a computer processor operatively connected with a machine-readable non-transitory medium embodying information indicative of instructions for causing the computer processor to perform operations comprising:
      generating measure values based on outputs from the first and second frequency counters when the sensor unit is at a cranial location;
      determining the cranial location at which the measured values are associated;
      retrieving, from the memory, control values associated with the cranial location;
      comparing the measured values to the control values to generate deltas;
      comparing the deltas to a positive threshold and a negative threshold associated with each cranial location to ascertain an exceedance, the exceedance having a sign and a magnitude; and outputting an indication based on the sign of the exceedance, and an indicator or display connected with the computer processor for the indications.

2. The apparatus of claim 1 wherein the operations further comprise:
combining an exceedance from the first sensor coil with an exceedance from the second sensor coil to generate the indication.

3. The apparatus of claim 1 wherein the indication includes the magnitude of the exceedance.

4. The apparatus of claim 1 further comprising:
a position gauge attached to the sensor unit,
wherein the determining of the cranial location at which the measured values are associate includes reading from the position gauge.

5. The apparatus of claim 4 further comprising:
a head-mounting frame including fiducial markers indicating cranial locations,
wherein the position gauge is configured to identify cranial locations based on the fiducial markers.

6. The apparatus of claim 5 further comprising:
an attachment point on the head-mounting frame configured to releasably connect with the sensor unit.

7. The apparatus of claim 6 wherein the attachment point is configured to guide the first and second coils of the sensor unit in a direction normal from a surface at the cranial location.

8. The apparatus of claim 1 further comprising:
an accelerometer or gyroscope connected with the sensor unit and configured to determine the cranial location at which each measured value is taken.

9. The apparatus of claim 1 wherein the operations further comprise:
generating a matrix of exceedances based on measured values from multiple cranial locations.

10. The apparatus of claim 9 wherein the operations further comprise:
rendering an image based on the matrix of exceedances.

11. The apparatus of claim 1 wherein the second sensor coil is coaxial around a common axis with the first sensor coil.

12. The apparatus of claim 1 wherein an exceedance based upon a frequency higher than a control value indicates a hemorrhagic stroke, and an exceedance based upon a frequency lower than a control value indicates an ischemic stroke.

13. A method of diagnosing an issue in a subject's brain, the method comprising:
reading a measured value from a first frequency counter on a first resistive, inductive, and capacitive (RLC) circuit connected with a first sensor coil;
reading a measured value from a second frequency counter on a second RLC circuit connected with a second sensor coil, the second sensor coil being coaxial around a common axis with the first sensor coil and having a larger or smaller diameter than the first sensor coil, the first and second sensor coils forming a sensor unit, the sensor unit held to a subject's head;
determining a cranial location at which the measured values are read;
retrieving, from a memory, control values associated with the cranial location;
comparing the measured values with the control values to generate deltas;
comparing each delta to a positive threshold and a negative threshold in order to ascertain an exceedance, the exceedance having a sign and a magnitude; and
indicating, to a user, a type of issue based on the sign of the exceedance.

14. The method of claim 13 further comprising:
indicating, to the user, the magnitude of the exceedance.

15. The method of claim 13 wherein the determining of the cranial location includes reading from a position gauge.

16. The method of claim 13 further comprising:
generating a matrix of exceedances corresponding to multiple cranial locations; and
rendering an image based on the matrix of the exceedances.

17. The method of claim 13 further comprising:
distinguishing between an ischemic and a hemorrhagic stroke based on the sign of the exceedance.

* * * * *